United States Patent
Dalko et al.

(10) Patent No.: US 6,964,954 B2
(45) Date of Patent: Nov. 15, 2005

(54) USE OF DHEA DERIVATIVES ON KERATINOUS SUBSTANCES

(75) Inventors: Maria Dalko, Gif S/Yvette (FR); Alexandre Cavezza, Tremblay-en-France (FR)

(73) Assignee: L'Oreal, Paris (FR)

( * ) Notice: Subject to any disclaimer, the term of this patent is extended or adjusted under 35 U.S.C. 154(b) by 103 days.

(21) Appl. No.: 10/279,852

(22) Filed: Oct. 25, 2002

(65) Prior Publication Data

US 2003/0113284 A1 Jun. 19, 2003

(30) Foreign Application Priority Data

Oct. 25, 2001 (FR) .......................................... 01 13817

(51) Int. Cl.⁷ .............................................. A61K 31/56
(52) U.S. Cl. ...................................... 514/178; 514/182
(58) Field of Search ................................ 514/178, 182

(56) References Cited

U.S. PATENT DOCUMENTS

| | | | |
|---|---|---|---|
| 5,714,481 A | * | 2/1998 | Schwartz et al. ........... 514/177 |
| 5,843,932 A | | 12/1998 | Labrie |
| 6,399,084 B1 | | 6/2002 | Zenk et al. |
| 2003/0054021 A1 | | 3/2003 | Dalko et al. |

FOREIGN PATENT DOCUMENTS

| | | |
|---|---|---|
| FR | 1 145 705 A2 | 10/2001 |
| WO | WO 98/40074 | 9/1998 |
| WO | WO 00/28996 | 5/2000 |
| WO | WO 01/23405 A2 | 4/2001 |
| WO | WO 03/035023 A1 | 5/2003 |

OTHER PUBLICATIONS

Ergosteroids II: Biologically active metabolites and synthetic derivatives of dehydroepiandrosterone, *Steroids*, 1998, vol. 63, Mar.

\* cited by examiner

*Primary Examiner*—Barbara P. Badio
(74) *Attorney, Agent, or Firm*—Oblon, Spivak, McClelland, Maier & Neustadt, P.C.

(57) ABSTRACT

Methods of improving the appearance of keratinous substances using at least one DHEA derivative such as the skin, hair, eyelashes and/or nails, in particular for preventing or treating cutaneous signs of ageing and/or a faded complexion and/or disorders of pigmentation of the skin or hair and/or drying of the skin and/or hyperseborrhoea and/or imperfections relating to hyperseborrhoea and/or sensitive skin and/or dandruff and/or hair loss and/or canities.

30 Claims, No Drawings

USE OF DHEA DERIVATIVES ON KERATINOUS SUBSTANCES

FIELD OF THE INVENTION

The present invention relates to the use of at least one DHEA derivative for improving the appearance of keratinous substances, such as the skin, hair, eyelashes and/or nails, in particular for preventing or treating cutaneous signs of ageing and/or a faded complexion and/or disorders of pigmentation of the skin or hair and/or drying of the skin and/or hyperseborrhoea and/or imperfections related to hyperseborrhoea and/or sensitive skin and/or dandruff and/or hair loss and/or canities.

The present invention also relates to a process for the treatment of keratinous substances comprising the topical application to the keratinous substances of a composition including at least one DHEA derivative in a physiologically acceptable medium.

BACKGROUND OF THE INVENTION

DHEA or dehydroepiandrosterone is a natural steroid produced essentially by the corticoadrenal glands. Exogenous DHEA, administered topically or orally, is known for its ability to promote keratinization of the epidermis (JP-07 196 467) and to treat dry skin by increasing the endogenous production and secretion of sebum, thus strengthening the barrier effect of the skin (U.S. Pat. No. 4,496,556). It has also been disclosed, in U.S. Pat. No. 5,843,932, to use DHEA for curing atrophy of the dermis by inhibition of the loss of collagen and of connective tissue. Finally, the ability of DHEA to control the papery appearance of the skin (FR 00/00349), to adjust the pigmentation of the skin and hair (FR 99/12773) and to combat atrophy of the epidermis (FR 00/06154) has been demonstrated. These properties of DHEA make it a candidate of choice as an antiageing active principle.

However, DHEA exhibits effects of a hormonal nature which can render its use problematic.

For this reason, attempts have been made to make available DHEA derivatives which exhibit similar advantageous properties to DHEA but which do not have hormonal effects.

DHEA derivatives already known include 3β-acetoxy-7-oxo-DHEA or Δ5-androstene-3β-acetoxy-7,17-dione, which has been disclosed as being effective in the modulation of the immune system (U.S. Pat. No. 5,292,730, U.S. Pat. No. 5,585,371, U.S. Pat. No. 5,641,766), the treatment of Alzheimer's disease (U.S. Pat. No. 5,707,983), the treatment of HIV syndrome (U.S. Pat. No. 5,885,977) and for promoting weight loss (U.S. Pat. No. 5,296,481, U.S. Pat. No. 5,807,848).

PCT patent application WO 99/25333 additionally mentions the use, in particular the topical use, of 3β-acetoxy-7-oxo-DHEA in the prophylactic and curative treatment of lupus erythematosus, which is a disorder of the immune system capable of affecting several organs and which is revealed in the skin by a transverse redness of the face and/or by squamous erythemal plaques disseminated over the body.

U.S. Pat. No. 5,424,463 discloses 7-keto-DHEA (or Δ5-androstene-3β-ol-7,17-dione) and its hydrolysable derivatives obtained by modification of the 3β-hydroxy group, the derivatives being capable of restoring 7-keto-DHEA after hydrolysis. The 3β-hydroxy group is converted to carbamate or is esterified with (i) a saturated or unsaturated and normal or branched $C_2$–$C_{22}$ aliphatic acid, (ii) a $C_7$–$C_{22}$ aromatic acid, (iii) a dicarboxylic acid comprising 3 or more carbon atoms, for which only one carbonyl group is esterified with the 3-hydroxy group of the steroid, or (iv) an inorganic acid, such as sulphuric acid and phosphoric acid. U.S. Pat. No. 5,424,463 discloses 7-keto-DHEA and its hydrolysable derivatives as being effective in promoting weight loss.

PCT patent application WO 98/40074 discloses the use of DHEA derivatives of formula (A):

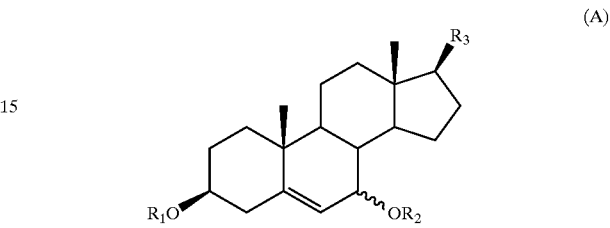

in which:
R$_1$ is chosen from: a hydrogen atom or the following functional groups: ester of organic acid comprising 1 to 24 carbon atoms, sulphuric ester or phosphoric ester, or carbonaceous ether comprising 1 to 24 carbon atoms comprising no or several nitrogen atoms, or ethers of carbohydrates comprising 3 to 100 carbon atoms and their derivatives comprising or not comprising one or more nitrogen atoms;
R$_2$ is chosen from: a hydrogen atom or an ester functional group of fatty acid comprising 1 to 24 carbon atoms;
R$_3$ is chosen from: a hydrogen atom, an —OH group or groups of formulae: —CO—R$_4$, —CHOH—R$_4$, =CH—CH$_3$, =COH—CH$_3$, —CHR$_4$—CH$_3$ or =O, in which groups R$_4$ is an alkyl group comprising from 1 to 10 carbon atoms which is or is not substituted;
in a composition for preventing or treating signs of cutaneous ageing and/or the effects of UV radiation on the skin.

PCT patent application WO 00/28996 discloses a composition for improving the texture of tissues comprising a DHEA derivative of formula (A) in combination with an elastin-derived peptide obtained by selective cleavage of elastin by thermolysin.

However, to Applicants' knowledge, it has never been suggested to use DHEA derivatives of general formula (I) for improving the appearance of keratinous substances, in particular in the treatment of signs of ageing.

SUMMARY OF THE INVENTION

The present invention relates to the use of at least one DHEA derivative for improving the appearance of keratinous substances, such as the skin, hair, eyelashes and/or nails, in particular for preventing or treating cutaneous signs of ageing and/or a faded complexion and/or disorders of pigmentation of the skin or hair and/or drying of the skin and/or hyperseborrhoea and/or imperfections related to hyperseborrhoea and/or sensitive skin and/or dandruff and/or hair loss and/or canities.

The present invention also relates to a process for the treatment of keratinous substances comprising the topical application to the keratinous substances of a composition including at least one DHEA derivative in a physiologically acceptable medium.

DETAILED DESCRIPTION OF THE INVENTION

The present invention relates to the use, preferably the cosmetic use, for improving the appearance of keratinous substances, of at least one DHEA derivative of following formula (I):

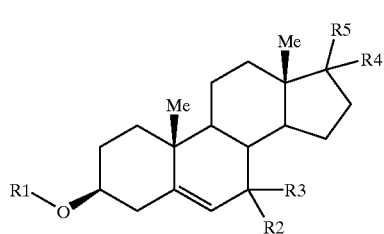

in which:
R1 is chosen from:
  a hydrogen atom;
  a saturated or unsaturated, linear or branched, or cyclic, which can optionally comprise one or more heteroatoms, $C_1$–$C_{12}$ alkyl group which is optionally substituted by one or more groups chosen from —OR' and/or —SR' and/or —COOR' and/or —NR'R' and/or halogen and/or perfluoroalkyl and/or sulphate and/or phosphate and/or aryl and/or heterocycle, the heterocycle advantageously being chosen from an indole, a pyrimidine, a piperidine, a morpholine, a pyran, a furan, a piperazine or a pyridine;
  an alkylcarbonyl group, the $C_1$–$C_{24}$ alkyl part of which is saturated or unsaturated, linear, branched or cyclic, and optionally substituted by one or more groups chosen from —OR' and/or —SR' and/or —COOR' and/or —NR'R' and/or halogen and/or perfluoroalkyl and/or sulphate and/or phosphate and/or aryl and/or heterocycle, the heterocycle advantageously being chosen from an indole, a pyrimidine, a piperidine, a morpholine, a pyran, a furan, a piperazine or a pyridine;
  a phenyl group, optionally functionalized by one or more —OR' and/or —SR' and/or —COOR' and/or —NR'R' and/or halogen and/or perfluoroalkyl and/or sulphate and/or phosphate and/or aryl and/or heterocycle groups;
  a benzyl group, optionally functionalized by one or more —OR' and/or —SR' and/or —COOR' and/or —NR'R' and/or halogen and/or perfluoroalkyl and/or sulphate and/or phosphate and/or aryl and/or heterocycle groups;
  an arylcarbonyl group, preferably a phenylcarbonyl, or an arylalkylcarbonyl group, preferably a benzylcarbonyl, optionally substituted by one or more —OR' and/or —SR' and/or —COOR' and/or —NR'R' and/or halogen and/or perfluoroalkyl and/or sulphate and/or phosphate and/or aryl and/or heterocycle groups;
  an O=P(OH)OR' group;
  an (O)$_2$SOR' group;
  an (O)$_2$SR' group;
  a trialkylsilyl group (SiR'$_3$) in which the R' groups may be identical or different;
  an alkyloxycarbonyl group (R'OCO);
  an alkylaminocarbonyl group (R'NR'''CO);
  a carbohydrate comprising 3 to 100 carbon atoms and their derivatives;
R4 and R5:
  together represent a group chosen from:
    a keto group (=O);
    a =CHR' group;
    an =NR' group;
    a =NCOR' group;
  each represent an identical —OR'' group;
  advantageously the two —OR'' groups together form a 1,3-dioxolane or 1,3-dioxane ring;
  each represent an identical or different group chosen from:
    a hydrogen atom;
    an —NR'R' group;
    an —NHCOR' group;
When R3 represents a hydrogen atom, R2 is chosen from:
  an —OR6 group in which R6 has the same definitions as those given above for R1;
  an amine group —N(R7)$_2$ in which the R7 substituents, which are identical or different, have the same definitions as those given above for R1;
  an N-sulphonamide group (—NR'''SO$_2$R') or an N-sulphonate group (—NR'''SO$_3$R'), preferably in the alkali metal salt form;
  a urea group (—NR'''CONR'R');
  an alkylamide group (—NR'''COR');
  an N-carbamate group (—NR'''COOR');
  a thiol group (—SR');
  a thiophenyl group (—SPh);
  a sulphone group (—SO$_2$R');
  a sulphoxide group (—SOR');
  a halogen;
  an alkylsilane group (—SiR'$_3$) in which the R' groups may be identical or different;
R2 and R3 can also together represent a group chosen from:
  a methylene (=CHR');
  an imine (=NHR');
  an oxime (=NOR');
  a hydrazone (=N—NR'R');
  a keto group (=O);
R2 and R3 can also each represent an —OR'' group in which each of the R'' groups represents $C_1$–$C_6$, preferably $C_1$–$C_3$, alkyl chains which together advantageously form a ring, preferably a 5-membered ring (1,3-dioxolane ring) or a 6-membered ring (1,3-dioxane ring);
R' is chosen from a hydrogen atom or a saturated or unsaturated, linear or branched, or cyclic, which can optionally comprise one or more heteroatoms, $C_1$–$C_{12}$, preferably $C_1$–$C_6$, alkyl group optionally substituted by one or more —OR''', —COOR''', halogen or —NR'''R''' groups; or by an aryl group, preferably a phenyl, optionally substituted by one or more —OR''', —COOR''', halogen or —NR'''R''' groups; preferably, R' represents a hydrogen atom, a methyl, an ethyl, a butyl, a propyl, an isopropyl or a tert-butyl group;
R''' represents a hydrogen atom or a saturated or unsaturated and linear, branched or cyclic alkyl chain, preferably $C_1$–$C_6$ alkyl chain; preferably, R''' represents a hydrogen atom, a methyl, an ethyl, a butyl, a propyl, an isopropyl or a tert-butyl group; it being understood that, in each of the —NR'R' and —NR'''R''' groups, the R' and R''' substituents respectively are identical or different;
with the exception of the DHEA derivatives of formula (I) for which:
  R2 and R3 together represent a keto group;
  R4 and R5 together represent a keto group; and
  R1 is as defined above;

with the exception of the DHEA derivatives of formula (A)

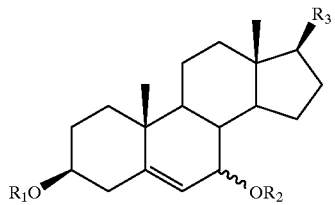
(A)

in which:
- R₁ is chosen from: a hydrogen atom or the following functional groups: ester of organic acid comprising 1 to 24 carbon atoms, sulphuric ester or phosphoric ester, or carbonaceous ether comprising 1 to 24 carbon atoms comprising no or several nitrogen atoms, or ethers of carbohydrates comprising 3 to 100 carbon atoms and their derivatives comprising or not comprising one or more nitrogen atoms;
- R₂ is chosen from: a hydrogen atom or an ester functional group of fatty acid comprising 1 to 24 carbon atoms;
- R₃ is chosen from: a hydrogen atom, an —OH group or groups of formulae: —CO—R₄, —CHOH—R₄, =CH—CH₃, =COH—CH₃, —CHR₄—CH₃ or =O, in which groups R₄ is an alkyl group comprising from 1 to 10 carbon atoms which is or is not substituted.

The present invention also relates to the optical and/or geometrical isomers of the DHEA derivatives of formula (I), alone or as a mixture in any proportions, and to the physiologically acceptable salts of these derivatives, and to their use for improving the appearance of keratinous substances as set forth herein.

The term "keratinous substances" is understood to mean preferably the skin, hair fibres (hair and eyelashes) and nails.

According to a preferred embodiment of the present invention, the preferred DHEA derivatives of formula (I) are those in which R1 represents a saturated or unsaturated, linear or branched, or cyclic, which can comprise one or more heteroatoms, C₁–C₆ alkyl group optionally substituted by one or more groups chosen from —OR' and/or —SR' and/or —COOR' and/or —NR'R' and/or halogen.

According to another preferred embodiment of the present invention, the preferred DHEA derivatives of formula (I) are those in which R1 represents an alkylcarbonyl group, the C₁–C₂₀, preferably C₆–C₁₈, alkyl part of which is saturated or unsaturated and linear, branched or cyclic and optionally substituted by one or more groups chosen from —OR' and/or —SR' and/or —COOR' and/or —NR'R' and/or halogen.

When R3 represents a hydrogen atom, R2 is preferably chosen from:
- an —OR6 group in which R6 has the same definitions as those given above in a preferred way for R1;
- an amine group —N(R7)₂ in which the R7 substituents, which are identical or different, have the same definitions as those given above in a preferred way for R1;
- a thiol group (—SR');
- a halogen.

According to another preferred embodiment of the present invention, the preferred DHEA derivatives of formula (I) are those in which each of the —NR'R' and/or —NR"'R'" groups represents an amino acid preferably chosen from L-alanine, L-arginine, L-asparagine, L-aspartic acid, L-cysteine, L-glutamine, L-glutamic acid, glycine, L-hixtidine, L-isoleucine, L-leucine, L-lysine, L-methionine, L-phenylalanine, L-proline, L-serine, L-threonine, L-tryptophan, L-tyrosine or L-valine.

Particularly preferred derivatives of formula (I) used according to the present invention include the following compounds:

Androst-5-en-17-one, 3-(acetyloxy)-7-(benzoyloxy)-, (3β, 7α);

Androst-5-en-17-one, 7-hydroxy-3-[[(1-oxopentyl)-sulphonyl]oxy]-, (3β, 7β);

Androst-5-en-17-one, 3-hydroxy-7-(1-oxo-3-phenylpropoxy)-, (3β, 7β);

Androst-5-en-17-one, 7-hydroxy-3-[[3-(4-hydroxy-3-methoxyphenyl)-1-oxo-2-propenyl]oxy]-, (3β);

Androst-5-en-17-one, 7-hydroxy-3-[[(9Z)-1-oxo-9-octadecenyl]oxy]-, (3β);

Pregn-5-en-20-one, 3-(acetyloxy)-7-hydroxy-, (3β, 7α);

Butanoic acid, 4-[[[(3β, 7Z)-3-hydroxy-17-oxoandrost-5-en-7-ylidene]amino]oxy]-;

Butanoic acid, 4-[[[(3β, 7Z)-3-(acetyloxy)-17-oxoandrost-5-en-7-ylidene]amino]oxy]-, methyl ester;

Androst-5-en-17-one, 3-(benzoyloxy)-7-(2-methyl-1-oxopropoxy)-, (3β, 7β);

Androst-5-en-17-one, 3-(acetyloxy)-7-fluoro-, (3β, 7β);

Androst-5-en-17-one, 3-(acetyloxy)-7-fluoro-, (3β, 7α);

Acetic acid, [[[(3β, 7Z)-3-hydroxy-20-oxopregn-5-en-7-ylidene]amino]oxy]-;

Acetic acid, [[[(3β, 7Z)-3-(acetyloxy)-20-oxopregn-5-en-7-ylidene]amino]oxy]-, methyl ester;

Androst-5-en-17-one, 3-(acetyloxy)-7-bromo-, (3β);

Androst-5-en-17-one, 7-bromo-3-hydroxy-, (3β, 7α);

Androst-5-en-17-one, 7-bromo-3-hydroxy-, (3β);

Pregn-5-en-20-one, 7-bromo-3-hydroxy-, acetate;

Pregn-5-en-20-one, 3-(acetyloxy)-7-bromo-, (3β);

Pregn-5-en-20-one, 7α-(-chloro-3β-hydroxy-, acetate;

Pregn-5-en-20-one, 3-(acetyloxy)-7-bromo-, (3β, 7β);

Pregn-5-en-20-one, 3-(acetyloxy)-7-bromo-, (3β, 7α);

Pregn-5-en-20-one, 7-bromo-3-hydroxy-, benzoate;

Pregn-5-en-20-one, 7-bromo-3β-hydroxy-, 4-methylvalerate;

Androst-5-en-17-one, 3β, 7α-dihydroxy-, disulphate;

Acetic acid, [[(3β, 7α)-3-hydroxy-17-oxoandrost-5-en-7-yl]thio]-;

Androst-5-ene-7,17-dione, 3-(acetyloxy)-, 7,17-dioxime, (3β);

Androst-5-en-17-one, 3-(benzoyloxy)-7-bromo-, (3β, 7α);

Acetic acid, [[[(3β, 7Z)-3-hydroxy-17-oxoandrost-5-en-7-ylidene]amino]oxy]-;

Acetic acid, [[[(3β, 7Z)-3-hydroxy-17-oxoandrost-5-en-7-ylidene]amino]oxy]-, methyl ester;

Acetic acid, [[[3β, 7Z)-3-(acetyloxy)-17-oxoandrost-5-en-7-ylidene]amino]oxy]-, methyl ester;

Androst-5-en-17-one, 3,7-bis[(trimethylsilyl)-oxy]-, (3β, 7β);

Androst-5-en-17-one, 7-hydroxy-3-[[(3-methyl-phenyl)sulphonyl]oxy]-, (3β, 7α);

Androst-5-en-17-one, 3-[(3-chlorobenzoyl)oxy]-7-hydroxy-, (3β, 7α);

Androst-5-en-17-one, 7-(3-carboxy-1-oxopropoxy)-3-[(1-oxoheptyl)oxy]-, (3β, 7α);

Pregn-5-en-20-one, 3,7-bis[(trimethylsilyl)oxy]-, (3β, 7α);

Androst-5-en-17-one, 3,7-bis[(trimethylsilyl)-oxy]-, (3β, 7α);

Acetic acid, [[[(3β)-3-hydroxy-17-oxoandrost-5-en-7-ylidene]amino]oxy]-;

Androst-5-en-17-one, 3-(acetyloxy)-7-methoxy-, (3β, 7α);

Androst-5-en-17-one, 3-(acetyloxy)-7-methoxy-, (3β, 7β);

Pregna-5,16-diene-7,20-dione, 3-(acetyloxy)-, 7,20-dioxime, (3β);

Androst-5-en-17-one, 3-(acetyloxy)-7-bromo-, (3β, 7α);

Pregn-5-en-20-one, 3β, 7α-dihydroxy-, 7-(hydrogen sulphate);

Androst-5-en-17-one, 3-hydroxy-7-(sulphooxy)-, (3β, 7α);

Pregn-5-ene-7,20-dione, 3-hydroxy-, bis[(aminoiminomethyl)hydrazone], (3β);

Guanidine, 1,1'-[(3β-hydroxypregn-5-ene-7,20-diylidene)dinitrilo]di-, dihydrochloride;

Androst-5-en-17-one, 7-bromo-3β-hydroxy-, benzoate;

Androst-5-en-17-one, 3-hydroxy-7-methoxy-, (3β, 7α);

Androst-5-en-17-one, 3-hydroxy-7-methoxy-, (3β, 7β);

Androst-5-en-7-one, 3-(acetyloxy)-17-(benzoyloxy)-, 7-[O-(phenylmethyl)oxime], (3β, 7E, 17β);

Androst-5-ene-3,7,17-triol, 17-(hydrogen sulphate), (3β, 7β, 17β);

Androst-5-en-7-one, 3,17-bis(acetyloxy)-, 7-[O-(3-hydroxypropyl)oxime], (3β, 7Z, 17β);

Propanoic acid, 3-[[[(3β, 7Z, 17β)-3,17-bis(acetyloxy)androst-5-en-7-ylidene]amino]oxy]-, methyl ester;

Propanoic acid, 3-[[[(3β, 7Z, 17β)-3,17-bis(acetyloxy)androst-5-en-7-ylidene]amino]oxy]-;

Androst-5-en-17-one, 7-(acetyloxy)-3-[[(1,1-dimethylethyl)dimethylsilyl]oxy]-, cyclic 17-(1,2-ethanediyl acetal), (3β, 7β);

Androst-5-en-7-one, 3-(acetyloxy)-17-[[(1,1-dimethylethyl)dimethylsilyl]oxy]-, cyclic 7-(1,2-ethanediyl acetal), (3β, 17β);

Androst-5-ene-7,17-diol, 3-[[(1,1-dimethylethyl)-diphenylsilyl]oxy]-, 17-octanoate, (3β, 7β, 17β);

Butanoic acid, 4-[[[(3β, 7Z, 17β)-3-(acetyloxy)-17-hydroxyandrost-5-en-7-ylidene]amino]oxy]-, methyl ester;

Androst-5-ene-3,7,17-triol, 17-acetate 3-benzoate, (3β, 7β, 17β);

Acetic acid, [[[(3β, 7Z, 17β)-3-(acetyloxy)-17-hydroxyandrost-5-en-7-ylidene]amino]oxy]-, methyl ester;

Androst-5-ene-3,7,17-triol, 3,17-diacetate 7-methanesulphonate, (3β, 17β);

Androst-5-ene-3,17-diol, 7-bromo-, diacetate, (3β, 7β, 17β);

Androst-5-ene-3,7,17-triol, 3-acetate 17-benzoate, (3β, 7α, 17β);

Androst-5-ene-3,7,17-triol, 3-acetate 17-benzoate, (3β, 7β, 17β);

Androst-5-ene-3,17-diol, 7-bromo-, (3β, 7α, 17β);

Androst-5-ene-3,17-diol, 7-bromo-, (3β, 17β);

Androst-5-ene-3,17-diol, 7-bromo-, 3-acetate 17-benzoate, (3β, 7α, 17β);

Androst-5-ene-3,17-diol, 7-(phenylsulphinyl)-, diacetate, (3β, 17β);

Androst-5-ene-3,17-diol, 7-(phenylthio)-, diacetate, (3β, 17β);

Androst-5-ene-3,17-diol, 7-bromo-, diacetate, (3β, 17β);

Androst-5-ene-3β, 17β-diol, 7-bromo-, dibenzoate;

Androst-5-ene-3,17-diol, 7-bromo-, 3-acetate 17-benzoate, (3β, 7β, 17β);

Propanoic acid, 3-[[(3β, 7α, 17β)-3-(acetyloxy)-17-(benzoyloxy)androst-5-en-7-yl]thio]-, methyl ester;

Propanoic acid, 3-[[(3β, 7α, 17β)-3,17-dihydroxyandrost-5-en-7-yl]thio]-;

Androst-5-en-7-one, 3-(acetyloxy)-17-(benzoyloxy)-, 7-[O-(phenylmethyl)oxime], (3β, 7Z, 17β);

Androst-5-ene-3,7,17-triol, 3-acetate 7,17-dibenzoate, (3β, 7α, 17β);

Androst-5-ene-3,7,17-triol, 3-acetate 7,17-dibenzoate, (3β, 7β, 17β);

Androst-5-en-17-one, 3-(acetyloxy)-7-bromo-, cyclic 1,2-ethanediyl acetal, (3β, 7β);

Androst-5-en-7-one, 3-(acetyloxy)-17-(benzoyloxy)-, 7-[O-(phenylmethyl)oxime], (3β, 17β);

Androst-5-en-17-one, 3,7-bis(acetyloxy)-, cyclic 17-(1,2-ethanediyl acetal), (3β, 7α);

Androst-5-en-17-one, 3-(acetyloxy)-7-hydroxy-, cyclic 17-(1,2-ethanediyl acetal), (3β, 7β);

Androst-5-en-17-one, 3-(acetyloxy)-7-hydroxy-, cyclic 17-(1,2-ethanediyl acetal), (3β, 7α);

Androst-5-ene-7,17-dione, 3-(acetyloxy)-, 7,17-dioxime, (3β);

Androst-5-en-3-ol, 7-bromo-, benzoate, (3β);

Androst-5-ene-7,17-dione, 3-(acetyloxy)-, 17-(1,2-ethanediyl acetal), 7-oxime, (3β, 7Z);

Acetic acid, [[[(3β, 7Z)-3-(acetyloxy)-17,17-[1,2-ethanediylbis(oxy)]androst-5-en-7-ylidene]amino]-oxy]-, methyl ester;

Androst-5-en-7-one, 3,17-bis[(trimethylsilyl)-oxy]-, O-methyloxime, (3β, 17β);

Androst-5-en-7-one, 3,17-dihydroxy-, oxime, (3β, 17β);

Androst-5-ene-7,17-dione, 3-(acetyloxy)-, 17-oxime, (3β);

Androst-5-ene-7,17-dione, 3-(acetyloxy)-, 7,17-dioxime, (3β);

Acetic acid, [[[(3β, 17β)-3,17-dihydroxyandrost-5-en-7-ylidene]amino]oxy]-;

Acetic acid, [[[(3β)-17,17-[1,2-ethanediylbis-(oxy)]-3-hydroxyandrost-5-en-7-ylidene]amino]-oxy]-;

Silane, [[(3β, 7α, 17β)-androst-5-ene-3,7,17-triyl]tris(oxy)]tris[trimethyl]-;

Benzenesulphonic acid, 4-methyl-, [(3β, 17β)-3,17-bis(acetyloxy)androst-5-en-7-ylidene]hydrazide;

Androst-5-en-7-one, 3,17-bis(acetyloxy)-, oxime, (3β, 17β);

Androst-5-en-17-one, 3-(acetyloxy)-7-bromo-, cyclic 1,2-ethanediyl acetal, (3β, 7α);

Androst-5-en-17-one, 7-bromo-3-hydroxy-, cyclic 1,2-ethanediyl acetal, (3β, 17α);

Androst-5-en-3β-ol, 7α-bromo-, acetate;

Androst-5-en-3β-ol, 7α-bromo-.

The DHEA derivatives of formula (I) according to the invention are readily accessible from a synthetic viewpoint, in particular by the use of one of the synthetic methods disclosed in Patents U.S. Pat. No. 5,424,463, FR-2 771 105, U.S. Pat. No. 5,869,709, U.S. Pat. No. 6,111,118, WO 94/085888 and WO 01/23405 and/or in the document Tetrahedron Letters, 1997, 38, 119–122, the disclosure of which is hereby incorporated by reference in their entirety.

More particularly, the present invention relates to the use, preferably the cosmetic use, of at least one DHEA derivative of formula (I) as defined above for preventing or treating cutaneous signs of ageing and/or a faded complexion and/or disorders of pigmentation of the skin or hair and/or drying of the skin and/or hyperseborrhoea and/or imperfections related to hyperseborrhoea and/or sensitive skin and/or dandruff and/or hair loss and/or canities.

The term "cutaneous signs of ageing" is understood to include at least wrinkles and fine lines, loss of firmness and/or of elasticity of the skin, cutaneous atrophy, a more uneven skin grain with presence of dilated pores, loss of radiance of the skin and/or pigmentary blemishes.

The term "sensitive skin" is understood to mean skin which has been characterized in Patent EP 0 680 749 B1, hereby incorporated by reference in its entirety, which shows that the symptoms related to sensitive skin consisted of more or less painful sensations experienced in a cutaneous region, such as smarting, pins and needles, itching or pruritus, burning sensations, redness, warming sensations, discomfort, stabbing pains, and the like. These symptoms may be displayed in response to various factors, such as, inter alia, sweat, friction, the emotions, foods, the wind, shaving, soap, surfactants, hard water with a high calcium concentration, temperature variations or wool.

According to another aspect of the present invention, a composition including, in a physiologically acceptable medium, at least one DHEA derivative of formula (I) as defined above and at least one compound chosen from: a desquamating agent, a moisturizing agent, a depigmenting or propigmenting agent, an antiglycation agent, an NO-synthase inhibitor, a 5α-reductase inhibitor, a lysyl and/or prolyl hydroxylase inhibitor, an agent which stimulates the synthesis of dermal or epidermal macromolecules and/or which prevents their decomposition, an agent which stimulates the proliferation of fibroblasts and keratinocytes and/or the differentiation of keratinocytes, a muscle relaxant, a compound which reduces irritation of neurogenic origin, an antimicrobial agent, a tightening agent, an agent for combating pollution or free radicals, or a soothing agent capable of inhibiting at least one enzyme chosen from phospholipases A2, lipoxygenases and/or human prostaglandin synthetases is provided.

The present invention also relates to a composition including, in a physiologically acceptable medium, at least one DHEA derivative of formula (I) as defined above and at least one UV screening agent chosen from UV-A and/or UV-B screening agents and/or at least one optionally coated inorganic pigment.

The term "physiologically acceptable medium" is understood to mean a medium compatible with the skin and/or its superficial growths.

According to preferred embodiments, the composition according to the present invention preferably includes from 0.00001% to 10% by weight of DHEA derivative of formula (I) as defined above with respect to the total weight of the composition. More preferably, this composition includes from 0.001% to 5% by weight of DHEA derivative of formula (I) as defined above with respect to the total weight of the composition.

Examples of the various compounds capable of being introduced into the composition according to the invention will now be described.

1. Desquamating and Moisturizing Agents

The term "desquamating agent" is understood to mean any compound capable of acting:

either directly on desquamation by promoting exfoliation, such as β-hydroxy acids, in particular salicylic acid and its derivatives (including 5-(n-octanoyl)salicylic acid); α-hydroxy acids, such as glycolic acid, citric acid, lactic acid, tartaric acid, malic acid or mandelic acid; urea; gentisic acid; oligofucoses; cinnamic acid; *Saphora japonica* extract; hydroxystilbenes, including in particular resveratrol;

or on the enzymes involved in desquamation or decomposition of the corneodesmosomes, such as glycosidases, stratum corneum chymotryptic enzyme (SCCE) or other proteases (for example, trypsin, chymotrypsin-like). Suitable agents also include, for example, agents which chelate inorganic salts: EDTA; N-acyl-N,N',N'-ethylenediaminetriacetic acid; aminosulphonic compounds and in particular N-(2-hydroxyethyl)piperazine-N'-2-ethanesulphonic acid (HEPES); 2-oxothiazolidine-4-carboxylic acid (procysteine) derivatives; derivatives of α-amino acids of glycine type (as disclosed in EP-0 852 949); honey; or sugar derivatives, such as O-octanoyl-6-D-maltose and N-acetylglucosamine.

The term "moisturizing agent" is understood to mean:

either a compound which acts on the barrier function, for the purpose of keeping the stratum corneum moisturized, or an occlusive compound. Examples of such agents include ceramides, sphingoid-based compounds, lecithins, glycosphingolipids, phospholipids, cholesterol and its derivatives, phytosterols (stigmasterol, β-sitosterol or campesterol), essential fatty acids, 1,2-diacylglycerol, 4-chromanone, pentacyclic triterpenes, petroleum jelly and lanolin;

or a compound which directly increases the water content of the stratum corneum, such as threalose and its derivatives, hyaluronic acid and its derivatives, glycerol, pentanediol, pidolates, serine, xylitol, sodium lactate, glyceryl polyacrylate, ectoin and its derivatives, chitosan, oligo- and polysaccharides, cyclic carbonates, N-lauroylpyrrolidonecarboxylic acid and N-α-benzoyl-L-arginine;

or a compound which activates the sebaceous glands, such as steroid derivatives (including DHEA) and vitamin D and its derivatives.

These compounds preferably represent from 0.001% to 30%, more preferably from 0.01 to 20%, of the total weight of the composition according to the present invention.

The composition according to the present invention comprising the above-mentioned desquamating and moisturizing agents is preferably intended for the prevention or the treatment of drying of the skin and in particular of xerosis.

2. Depigmenting or Propigmenting Agents

The depigmenting agents capable of being incorporated in the composition according to the present invention comprise, for example, the following compounds: kojic acid; ellagic acid, arbutin and its derivatives, such as those disclosed in EP-895 779 and EP-524 109; hydroquinone; aminophenol derivatives such as those disclosed in PCT patent applications WO 99/10318 and WO 99/32077, in particular N-cholesteryloxycarbonyl-para-aminophenol and N-ethyloxycarbonyl-para-aminophenol; iminophenol derivatives, in particular those disclosed in PCT patent application WO 99/22707; L-2-oxothiazolidine-4-carboxylic acid or procysteine, and its salts and esters;

ascorbic acid and its derivatives, in particular ascorbyl glucoside; and plant extracts, in particular of liquorice, of blackberry and of skull cap, without this list being limiting.

Examples of suitable propigmenting agents include the extracts of burnet (*Sanguisorba officinalis*) sold by Maruzen, and extracts of chrysanthemum (*Chrysanthemum morifolium*).

The composition according to the present invention comprising the abovementioned depigmenting agents is preferably intended for the prevention or the treatment of hyperpigmentation, in particular of pigmentary blemishes related to ageing of the skin.

The composition including the above-mentioned propigmenting agents is preferably intended for the treatment of canities.

3. Antiglycation Agent

The term "antiglycation agent" is understood to mean a compound which prevents and/or reduces the glycation of skin proteins, in particular of dermal proteins, such as collagen.

Examples of suitable antiglycation agents include plant extracts of the Ericaceae family, such as an extract of blueberry (*Vaccinium angustifolium*); ergothioneine and its derivatives; and hydroxystilbenes and their derivatives, such as resveratrol and 3,3',5,5'-tetrahydroxystilbene. Suitable antiglycation agents of this type are disclosed in Applications FR 99/16166, FR 00/08158, FR 99/09267 and FR 99/16168, respectively. Resveratrol is particularly preferred for use in this invention.

The composition according to the invention comprising an antiglycation agent as defined above is preferably used to prevent or treat signs of cutaneous ageing, in particular to prevent or treat loss of tonicity and/or of elasticity of the skin.

4. NO-Synthase Inhibitor

Examples of NO-synthase inhibitors suitable for use in the present invention include a plant extract of the species *Vitis vinifera* which is sold in particular by Euromed under the name Leucocyanidines de raisins extra, or by Indena under the name Leucoselect®, or, finally, by Hansen under the name Extrait de marc de raisin; a plant extract of the species *Olea europaea* which is preferably obtained from olive tree leaves and which is sold in particular by Vinyals in the dry extract form or by Biologia & Technologia under the trade name Eurol BT; and a plant extract of the species *Gingko biloba* which is preferably a dry aqueous extract of this plant sold by Beaufour under the trade name Ginkgo biloba extrait standard.

The composition according to the invention comprising an NO-synthase inhibitor as defined above is preferably used to prevent or treat signs of cutaneous ageing and/or sensitive skin.

5. 5α-Reductase Inhibitor

When the composition according to the invention comprises a 5α-reductase inhibitor, suitable such inhibitors include, for example, retinoids and in particular retinol;
sulphur and sulphur derivatives;
zinc salts, such as zinc lactate, gluconate, pidolate, carboxylate, salicylate and/or cysteate;
selenium chloride;
vitamin B6 or pyridoxine;
the mixture of capryloyl glycine, of sarcosine and of extract of *Cinnamomum zeylanicum* sold in particular by Seppic under the trade name Sepicontrol A5®;
an extract of *Laminaria saccharina*, sold in particular by Secma under the trade name Phlorogine®;
an extract of *Spiraea ulmaria*, sold in particular by Silab under the trade name Sebonormine®;
plant extracts of the species *Arnica montana*, *Cinchona succirubra*, *Eugenia caryophyllata*, *Humulus lupulus*, *Hypericum perforatum*, *Mentha piperita*, *Rosmarinus officinalis*, *Salvia officinalis* and *Thymus vulgaris*, all sold, for example, by Maruzen;
an extract of *Serenoa repens* sold in particular by Euromed;
plant extracts of the genus *Silybum*;
plant extracts comprising sapogenins and in particular extracts of *Dioscorea* species rich in diosgenin or hecogenin; and
extracts of *Eugenia caryophyllata* comprising eugenol or eugenyl glucoside.

The 5α-reductase inhibitor preferably is present from 0.001% to 10%, more preferably from 0.01 to 5%, of the total weight of the composition according to the present invention. When the composition includes such a compound, it is particularly well suited to preventing or treating seborrhoea and/or hirsutism and/or androgen-dependent alopecia.

6. Lysyl and/or Prolyl Hydroxylase Inhibitor

Preferred examples of lysyl and/or prolyl hydroxylase inhibitors which can be used in the composition according to the present invention include 2,4-diaminopyrimidine 3-oxide or 2,4-DPO, disclosed in PCT patent application WO 96/09048, and 2,4-diamino-6-piperidinopyrimidine 3-oxide or "Minoxidil", disclosed in U.S. Pat. Nos. 4,139,619 and 4,596,812.

Preferably, these compounds are present in the composition according to the present invention at a level of 0.001 to 5% by weight, more preferably at a level of 0.01 to 5% by weight, with respect to the total weight of the composition.

The composition including the lysyl and/or prolyl hydroxylase inhibitor and the DHEA derivative of formula (I) according to the invention is preferably used in the treatment of alopecia.

7. Agent which Stimulates the Synthesis of Dermal or Epidermal Macromolecules and/or which Prevents their Decomposition Suitable active principles which stimulate dermal macromolecules include, for example, those which act:

either on the synthesis of collagen, such as extracts of *Centella asiatica*; asiaticosides and derivatives; ascorbic acid or vitamin C and its derivatives, synthetic peptides, such as iamine, biopeptide CL or the palmitoyloligopeptide sold by Sederma; peptides extracted from plants, such as the soybean hydrolysate sold by Coletica under the trade name Phytokine®; or plant hormones, such as auxins and cinnamic acid and its derivatives, as disclosed in the European patent application published under the number 0 925 779;

or on the synthesis of elastin, such as the extract of *Saccharomyces cerevisiae* sold by LSN under the trade name Cytovitin®; and the extract of the alga *Macrocystis pyrifera* sold by Secma under the trade name Kelpadelie®;

or on the synthesis of glycosaminoglycans, such as the product of fermentation of milk by *Lactobacillus vulgaris* sold by Brooks under the trade name Biomin yogourth®; the extract of the brown alga *Padina pavonica* sold by Alban Müller under the trade name HSP3®; and the extract of *Saccharomyces cerevisiae* available in particular from Silab under the trade name Firmalift® or from LSN under the trade name Cytovitin®;

or on the synthesis of fibronectin, such as the extract of Salina zooplankton sold by Seporga under the trade name GP4G®; the yeast extract available in particular from Alban Müller under the trade name Drieline®; and the palmitoyl pentapeptide sold by Sederma under the trade name Matrixil®;

or on the inhibition of metalloproteinases (MMP), such as more particularly MMP 1, 2, 3 or 9. Suitable examples of such compounds include retinoids and derivatives; isoflavonoids; oligopeptides and lipopeptides, lipoamino acids; the malt extract sold by Coletica under the trade name Collalift®; extracts of blueberry or of rosemary; carotenoids, including in particular lycopene; or isoflavones, their derivatives or the plant extracts comprising them, in particular extracts of soybean (sold, for example, by Ichimaru Pharcos under the trade name Flavosterone SB®), of red clover, of flax, of kakkon or of sage (as disclosed in the French Patent Application Number 00 10203);

or on the inhibition of serine proteases, such as leukocyte elastase or cathepsin G. Suitable examples of such compounds include the peptide extract of *Leguminosae* (*Pisum sativum*) seeds sold by LSN under the trade name Parelastyl®; and heparinoids and pseudodipeptides.

Preferred active principles which stimulate epidermal macromolecules include, for example, filaggrin and keratins, of the extract of lupin sold by Silab under the trade name Structurine®; the extract of beech *Fagus sylvatica* buds sold by Gattefossé under the trade name Gatuline®; and the extract of Salina zooplankton sold by Seporga under the trade name GP4G®.

The composition according to the present invention including one or more of the above compounds is particularly well suited to use in the prevention or the treatment of cutaneous signs of ageing, in particular of loss of firmness and/or of elasticity of the skin.

8. Agent which Stimulates the Proliferation of Fibroblasts or Keratinocytes and/or the Differentiation of Keratinocytes Examples of agents which stimulate the proliferation of fibroblasts which can be used in the composition according to the present invention include plant proteins or polypeptides, extracts, in particular of soybean (for example, a soybean extract sold by LSN under the name Eleseryl SH-VEG 8® or sold by Silab under the trade name Raffermine®); and plant hormones, such as gibberellins and cytokinins.

Examples of agents which stimulate the proliferation of keratinocytes which can be used in the composition according to the present invention include retinoids, such as retinol and its esters, including retinyl palmitate; the extracts of walnut meal sold by Gattefossé; and the extracts of *Solanum tuberosum* sold by Sederma.

Example of agents which stimulate the differentiation of keratinocytes include inorganic materials, such as calcium; the extract of lupin sold by Silab under the trade name Photopréventine®; sodium β-sitosteryl sulphate, sold by Seporga under the trade name Phytocohésine®; and the extract of maize sold by Solabia under the trade name Phytovityl®.

The composition according to the present invention comprising these compounds is preferably intended to be used to prevent or treat cutaneous signs of ageing.

9. Muscle Relaxant

Examples of muscle relaxants which can be used in the composition according to the present invention include calcium inhibitors, such as alverine and its salts, chloride-channel openers, such as diazepam, and inhibitors of catecholamines and of acetylcholine, such as the hexapeptide argireline R sold by Ilipotec.

The composition according to the present invention comprising these compounds is preferably intended to be used to prevent or treat cutaneous signs of ageing and in particular wrinkles.

10. Antimicrobial Agent

Examples of antimicrobial agents capable of being used in the composition according to the present invention include 2,4,4'-trichloro-2'-hydroxydiphenyl ether (or triclosan), 3,4,4'-trichlorocarbanilide, phenoxyethanol, phenoxypropanol, phenoxyisopropanol, hexamidine isethionate, metronidazole and its salts, miconazole and its salts, itraconazole, terconazole, econazole, ketoconazole, saperconazole, fluconazole, clotrimazole, butoconazole, oxiconazole, sulfaconazole, sulconazole, terbinafin, ciclopirox, ciclopiroxolamine, undecylenic acid and its salts, benzoyl peroxide, 3-hydroxybenzoic acid, 4-hydroxybenzoic acid, phytic acid, N-acetyl-L-cysteine, lipoic acid, azelaic acid and its salts, arachidonic acid, resorcinol, 2,4,4'-trichloro-2'-hydroxydiphenyl ether, 3,4,4'-trichlorocarbanalide, octopirox, octoxyglycerin, octanoylglycine, caprylyl glycol, 10-hydroxy-2-decanoic acid, dichlorophenylimidazole dioxolane and its derivatives disclosed in Patent WO 93/18743, farnesol, phytosphingosines and their mixtures.

The preferred antimicrobial agents are triclosan, phenoxyethanol, octoxyglycerin octanoylglycine, 10-hydroxy-2-decanoic acid, caprylyl glycol, farnesol and azelaic acid.

Preferably, the antimicrobial agent can be used in the composition according to the present invention in an amount representing from 0.1 to 20%, more preferably from 0.1 to 10%, of the total weight of the composition.

The composition including the DHEA derivative of formula (I) and the antimicrobial agent is particularly well suited to use in the treatment of greasy skin with a tendency towards acne, acne or dandruff of the scalp.

11. Tightening Agent

The term "tightening agent" is understood to mean a compound capable of exerting tension on the skin, the effect of which is to temporarily render less distinct unevennesses in the surface of the skin, such as wrinkles and fine lines.

Examples of suitable tightening agents which can be used in the composition according to the present invention include:

(1) polyurethane latices or acrylic-silicone latices, in particular those disclosed in Patent Application EP-1 038 519, such as a polydimethylsiloxane grafted with propylthio[poly(methyl acrylate)], propylthio-[poly (methyl methacrylate)] and propylthio[poly-(methacrylic acid)] or a polydimethylsiloxane grafted with propylthio [poly(isobutyl methacrylate)] and propylthio[poly (methacrylic acid)]. Such grafted silicone polymers are sold, for example, by 3M under the trade names VS 80, VS 70 or LO21.

(2) soybean or wheat plant proteins, and/or (3) sodium magnesium silicates (Laponites).

The compositions according to the present invention comprising the above tightening agents are advantageously intended for the treatment of cutaneous signs of ageing, in particular of wrinkles and fine lines.

12. Agent for Combating Pollution or Free Radicals

The expression "agent for combating pollution" is understood to mean any compound capable of trapping ozone, mono- or polycyclic aromatic compounds, such as benzopyrene, and/or heavy metals, such as cobalt, mercury, cadmium and/or nickel. The term "agent for combating free radicals" is understood to mean any compound capable of trapping free radicals.

Suitable examples of ozone-trapping agents which can be used in the composition according to the present invention include vitamin C and its derivatives, including ascorbyl glucoside; phenols and polyphenols, in particular tannins, ellagic acid and tannic acid; epigallocatechin and the natural extracts comprising it; extracts of olive tree leaf; extracts of tea, in particular of green tea; anthocyans; extracts of rosemary; phenol acids, in particular chlorogenic acid; stilbenes, in particular resveratrol; sulphur-comprising amino acid derivatives, in particular S-carboxymethylcysteine; ergothioneine; N-acetyl-cysteine; chelating agents, such as N,N'-bis(3,4,5-trimethoxybenzyl)ethylenediamine or one of its salts, metal complexes or esters; carotenoids, such as crocetin; and various starting materials, such as the mixture of arginine, histidine ribonucleate, mannitol, adenosine triphosphate, pyridoxine, phenylalanine, tyrosine and hydrolysed RNA sold by Laboratoires Sérobiologiques under the trade name CPP LS 2633-12F®, the water-soluble fraction of maize sold by Solabia under the trade name Phytovityl®, the mixture of extract of fumitory and extract of lemon sold under the name Unicotrozon C-49® by Induchem, and the mixture of extracts of ginseng, of apple, of peach, of wheat and of barley sold by Provital under the trade name Pronalen Bioprotect®.

Suitable examples of agents which trap mono- or polycyclic aromatic compounds which can be used in the composition according to the present invention include tannins, such as ellagic acid; indole derivatives, in particular indole-3-carbinol; extracts of tea, in particular of green tea; extracts of water hyacinth or *Eichhornia crassipes*; and the water-soluble fraction of maize sold by Solabia under the trade name Phytovityl®.

Finally, suitable examples of agents which trap heavy metals which can be used in the composition according to the present invention include chelating agents, such as EDTA, the pentasodium salt of ethylenediaminetetramethylenephosphonic acid, and N,N'-bis(3,4,5-trimethoxybenzyl)ethylenediamine or one of its salts, metal complexes or esters; phytic acid; chitosan derivatives; extracts of tea; in particular of green tea; tannins, such as ellagic acid; sulphur-comprising amino acids, such as cysteine; extracts of water hyacinth (*Eichhornia crassipes*) and the water-soluble fraction of maize sold by Solabia under the trade name Phytovityl®.

The agents for combating free radicals which can be used in the composition according to the present invention can also comprise, in addition to some agents for combating pollution mentioned above, vitamin E and its derivatives, such as tocopheryl acetate; bioflavonoids; coenzyme Q10 or ubiquinone; certain enzymes, such as catalase, superoxide dismutase, lactoperoxidase, glutathione peroxidase and quione reductases; glutathione, benzylidenecamphor; benzylcyclanones; substituted naphthalenones; pidolates; phytanthriol; γ-oryzanol; lignans; and melatonin.

The compositions according to the present invention comprising the above agents for combating pollution and/or for combating free radicals are preferably intended for the prevention or the treatment of cutaneous signs of ageing, in particular of wrinkles and of loss of firmness and of elasticity of the skin and of dehydration. Also, they can be intended for the prevention or the treatment of a faded complexion.

13. UVA and/or UVB Screening Agent and Optionally Coated Inorganic Pigments

The composition according to the present invention can include one or more UV screening agents capable of screening out UVA and/or UVB radiation.

Suitable examples of compounds capable of screening out UVA radiation include:

(1) benzophenone derivatives, for example:

2,4-dihydroxybenzophenone (benzophenone-1);

2,2',4,4'-tetrahydroxybenzophenone (benzophenone-2);

2-hydroxy-4-methoxybenzophenone (benzophenone-3), available from BASF under the trade name Uvinul M40;

2-hydroxy-4-methoxybenzophenone-5-sulphonic acid (benzophenone-4) and its sulphonate form (benzophenone-5), available from BASF under the trade name Uvinul MS40;

2,2'-dihydroxy-4,4'-dimethoxybenzophenone (benzophenone-6);

5-chloro-2-hydroxybenzophenone (benzophenone-7);

2,2'-dihydroxy-4-methoxybenzophenone (benzophenone-8);

the disodium salt of 2,2'-dihydroxy-4,4'-dimethoxybenzophenone-5,5'-disulphonic diacid (benzophenone-9);

2-hydroxy-4-methoxy-4'-methylbenzophenone (benzophenone-10);

benzophenone-11;

2-hydroxy-4-(octyloxy)benzophenone (benzophenone-12);

benzophenone-3 and benzophenone-5 being preferred;

(2) triazine derivatives and in particular 2,4-bis[4-(2-ethylhexyloxy)-2-hydroxyphenyl]-6-(4-methoxyphenyl)-1,3,5-triazine, available from Ciba-Geigy under the trade name Tinosorb S and 2,2'-methylenebis[6-(2H-benzotriazol-2-yl)-4-(1,1,3,3-tetramethylbutyl)phenol], available from Ciba-Geigy under the trade name Tinosorb M;

(3) benzene-1,4-di(3-methylidenecamphor-10-sulphonic acid), optionally in the partially or completely neutralized form, and (4) their mixtures.

Suitable examples of compounds capable of filtering out UVB radiation include:

(1) salicylic acid derivatives, in particular homomenthyl salicylate and octyl salicylate;

(2) cinnamic acid derivatives, in particular 2-ethylhexyl 2-methoxycinnamate, available from Givaudan under the trade name Parsol MCX;

(3) liquid β,β-diphenylacrylate derivatives, in particular 2-ethylhexyl α-cyano-α,β-diphenylacrylate, or octocrylene, available from BASF under the trade name Uvinul N539;

(4) p-aminobenzoic acid derivatives;

(5) 4-methylbenzylidenecamphor, available from Merck under the trade name Eusolex 6300;

(6) 2-phenylbenzimidazole-5-sulphonic acid, sold under the trade name "Eusolex 232" by Merck;

(7) 1,3,5-triazine derivatives, in particular:

2,4,6-tris[p-(2'-ethylhexyl-1'-oxycarbonyl)-anilino]-1,3,5-triazine, available from BASF under the trade name Uvinul T150, and the compound corresponding to the following formula (A):

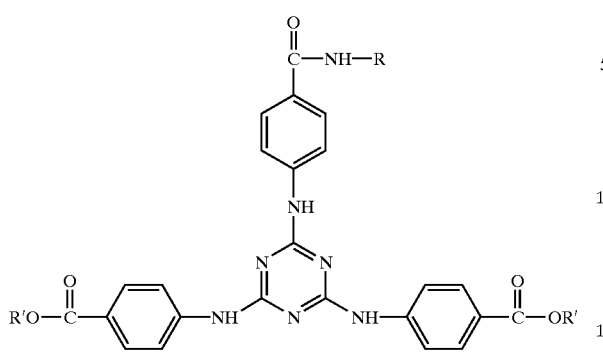

(A)

in which R' denotes a 2-ethylhexyl radical and R denotes a tert-butyl radical, available from Sigma 3V under the trade name Uvasorb HEB;

(8) their mixtures.

Suitable examples of compound capable of screening out UVA and UVB radiation include: (1) plant extracts, in particular of rosemary (rosmaric acid) and of the *Leontopodium* genus, in particular a plant species chosen from *Leontopodium alpinum* or *Leontopodium stracheyi;*

(2) the benzotriazole silicone corresponding to the following general formula (B):

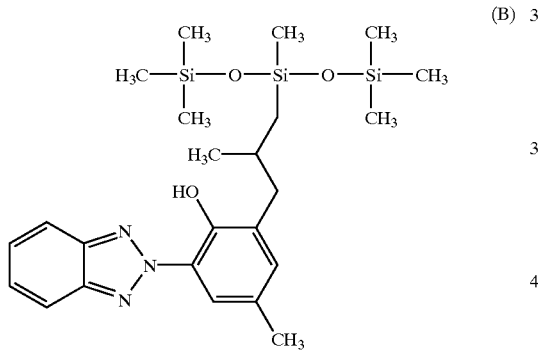

(B)

This benzotriazole silicone and its method of preparation are disclosed in particular in Application FR-A-2 642 968.

Suitable examples of optionally coated inorganic pigments include nanopigments comprising titanium oxide, iron oxide, zinc oxide, zirconium oxide or cerium oxide which are optionally coated with alumina and/or aluminium stearate.

14. Compounds which Reduce Irritation of Neurogenic Origin

Suitable examples of compounds which reduce irritation of neurogenic origin include:

substance P antagonists and in particular those mentioned in Patent EP 0 680 749, extracts of at least one non-photosynthetic filamentous bacterium, particularly of the strains of *Vitreoscilla filiformis* disclosed in Patent EP 0 761 204, the thermal waters disclosed in Patent EP 0 764 440, extracts of at least one plant of the family of the Rosaceae, particularly of the species *Rosa gallica*, disclosed in the European Patent Application published under the number No. 0 906 752, and the alkaline earth metals disclosed in the European Patent Applications published under the numbers 0 737 471 and 0 770 392;

CGRP antagonists, in particular those mentioned in Patent EP 0 765 668 and in particular extracts of members of the Iridaceae family, particularly of the species *Iris pallida;*

NO-synthase inhibitors;

bradykinin antagonists and in particular those mentioned in the European Patent Application published under the number 0 909 556;

cytokine antagonists;

histamine antagonists;

antagonists of interleukin 1 and/or of tumour necrosis factor α (TNF-α) and in particular those mentioned in the European Patent Applications published under the numbers 0 892 642 and 0 764 444, particularly the peptide Modulene, the tripeptide Lysine-Proline-Valine (KPV) and an extract of at least one plant of the family of the Labitae, particularly of the species *Rosmarinus officinalis;* sodium-channel blockers chosen in particular from: amiloride, quinidine, quinidine sulphate, apamine, cyproheptadine, loperamide and N-acetylprocainamide;

potassium-channel openers and in particular minoxidil and its derivatives.

15. Soothing Agents Capable of Inhibiting at Least One Enzyme

Examples of suitable soothing agents capable of inhibiting at least one enzyme chosen from phospholipases A2, lipoxygenases and/or human prostaglandin synthetases include:

pentacyclic triterpenes and plant extracts (in particular of *Glycyrrhiza glabra*) comprising, especially oleanolic acid and its salts, β-glycyrrhetinic acid and its salts and/or its derivatives, such as glycyrrhetic acid monoglucuronide, stearyl glycyrrhetinate or 3-stearoyloxyglycyrrhetic acid;

betulinic acid and its salts;

extracts of *Paeonia suffruticosa;* extracts of *Paeonia lactiflora;* calophyllum oil;

phycosaccharides, in particular Hydrolysed Algin® or Hydrolysed Algin and Zinc Sulfate® from Codif;

canola oil;

tamanu oil;

α-bisabolol;

extracts of camomile;

allantoin;

the phosphoric diester of vitamin E and C, in particular Sépivital EPC® from Seppic;

omega-3 unsaturated oils, such as musk rose oils, blackcurrant seed oils, echium oils or fish oils;

extracts of plankton, in particular Omega plancton® from Secma;

the combination of sodium palmitoylproline and of *Nymphaea alba*, in particular Seppicalm VG® from Seppic;

extracts of *Pygeum;* extracts of *Boswellia serrata*, in particular Soothex® from Quest;

extracts of *Centipeda cunnighamii*, in particular Phytoplenolin® from BioBotanica;

extracts of *Helianthus annuus*, in particular Hélioxine® from Silab;

extracts of *Linum usitatissimum*, in particular Sensiline® from Silab;

tocotrienols;

extracts of *Cola nitida;* piperonal;

extracts of clove;

extracts of rosebay willow-herb (*Epilobium angustifolium*);

extracts of *Aloe vera;* cortisone;

hydrocortisone;

indomethacin;

betamethasone.

In addition to the compound or compounds described above, the composition according to the present invention generally includes an effective amount of DHEA derivatives of formula (I) as defined above, which is sufficient to produce the desired effect. It thus comprises, for example, from 0.00001% to 10% by weight of the DHEA derivative of formula (I) with respect to the total weight of the composition, preferably from 0.001% to 5% by weight of the DHEA derivative of formula (I) with respect to the total weight of the composition, and more preferably from 0.1 to 0.5% by weight of the DHEA derivative of formula (I) with respect to the total weight of the composition.

The compositions according to the present invention may be intended for a cosmetic or pharmaceutical application, particularly a dermatological application. Preferably, the compositions according to the present invention are intended for a cosmetic application.

The compositions according to the present invention can be used for cosmetic purposes, for improving the appearance of keratinous substances, in particular for preventing or treating cutaneous signs of ageing and/or a faded complexion and/or disorders of pigmentation of the skin or of the hair and/or drying of the skin and/or hyperseborrhoea and/or imperfections related to hyperseborrhoea and/or sensitive skin and/or dandruff and/or hair loss and/or canities.

The compositions according to the invention are preferably suitable for topical application to keratinous substances, such as the skin, hair, eyelashes or nails. They can be provided in any pharmaceutical dosage form normally used for this type of application, for example, in the form of an aqueous or oily solution, or an oil-in-water or water-in-oil emulsion, of a silicone emulsion, of a microemulsion or nanoemulsion, of an aqueous or oily gel or of a liquid, pasty or solid anhydrous product.

These compositions can be more or less fluid and have the appearance of a white or coloured cream, of an ointment, of a milk, of a lotion, of a serum, of a paste, of a foam or of a gel. They can also be applied to the skin in the form of an aerosol, patch or powder. They can also be provided in the solid form, for example in the form of a stick. They can be used as product for caring for and/or as product for making up the skin. Also, they can be provided in the form of a shampoo or conditioner.

The composition of the present invention can also comprise the adjuvants which are standard in the cosmetics field, such as, for example, hydrophilic or lipophilic gelling agents, preservatives, antioxidants, solvents, fragrances, fillers, pigments, odour absorbers and colouring materials. The amounts of these various adjuvants are those conventionally used in the field under consideration, for example, from 0.01 to 20% of the total weight of the composition. These adjuvants, depending on their nature, can be introduced into the fatty phase or into the aqueous phase. These adjuvants, and their concentrations, must be such that they do not harm the advantageous properties of the DHEA derivative of formula (I) according to the present invention.

When the composition according to the invention is an emulsion, the proportion of the fatty phase preferably ranges from 2 to 80% by weight, more preferably from 5 to 50%, by weight with respect to the total weight of the composition. The fatty substances, the emulsifiers and the coemulsifiers used in the composition in the form of an emulsion are chosen from those conventionally used in the field under consideration. The emulsifier and the coemulsifier are preferably present in the composition in a proportion ranging from 0.3 to 30% by weight, more preferably from 0.5 to 20% by weight, with respect to the total weight of the composition.

Examples of suitable fatty substances which can be used in the invention include oils and in particular mineral oils (liquid petrolatum), oils of vegetable origin (avocado oil, soybean oil), oils of animal origin (lanolin oil), synthetic oils (perhydrosqualene), silicone oils (cyclomethicone) and fluorinated oils (perfluoropolyethers). Use may also be made, as fatty substances, of fatty alcohols, such as cetyl alcohol, of fatty acids, of waxes and of gums and in particular silicone gums.

Examples of suitable emulsifiers and coemulsifiers which can be used in the invention include, for example, esters of fatty acid and of polyethylene glycol, such as PEG-100 stearate, PEG-50 stearate and PEG-40 stearate; esters of fatty acid and of polyol, such as glyceryl stearate, sorbitan tristearate and oxyethylenated sorbitan stearates available under the trade names Tween® 20 or Tween® 60, for example; and their mixtures.

Suitable examples of hydrophilic gelling agents include carboxyvinyl polymers (carbomer), acrylic copolymers, such as acrylate/alkyl acrylate copolymers, polyacrylamides, polysaccharides, clays and natural gums. Suitable examples of lipophilic gelling agents include modified clays, such as bentones, metal salts of fatty acids and hydrophobic silica.

The present invention also relates to a process for the cosmetic treatment of keratinous substances comprising the topical application to the keratinous substances of a composition including, in a physiologically acceptable medium, at least one DHEA derivative of formula (I) as defined above, alone or in combination with at least one compound as described above.

The present invention also relates to a process for the cosmetic treatment of cutaneous signs of ageing and/or a faded complexion and/or disorders of pigmentation of the skin or of the hair and/or drying of the skin and/or hyperseborrhoea and/or imperfections related to hyperseborrhoea and/or sensitive skin and/or dandruff and/or hair loss and/or canities, comprising the topical application to the skin or hair of a composition including, in a physiologically acceptable medium, at least one DHEA derivative of formula (I) as defined above, alone or in combination with at least one compound as described above.

The present invention will now be illustrated by the following nonlimiting examples. In the composition examples, the amounts are indicated as percentage by weight.

EXAMPLES

Example 1

Moisturizing Cream

| Phase A | | |
|---|---|---|
| Acrylate/$C_{10-30}$ acrylate copolymer | | 0.5% |
| Water | | 12.0% |
| Phase B | | |
| Hydrogenated polyisobutene | | 5.0% |
| Androst-5-en-17-one, 3-(acetyloxy)-7-methoxy-, (3β, 7α) | | 0.1% |
| Cyclohexasiloxane | | 6.0% |
| Phase C | | |
| Triethanolamine | | 1.0% |
| Glycerol | | 6.0% |
| EDTA | | 0.2% |
| Preservatives | | 0.5% |
| Glycine | | 2.0% |
| Polyacrylamide and $C_{13-14}$ isoparaffin and laureth-7 | | 1.0% |
| Water | q.s. for | 100% |

This composition can be prepared in the following way. The polymer of phase A is dispersed in water at 40° C. The constituents of phase B are heated at 70° C. until completely dissolved and then the temperature is brought back to 40° C. The constituents of phase C are mixed at 50° C. Phase B is subsequently introduced into phase A at 40° C. with stirring and then phase C is added to them.

The above composition makes it possible to remoisturize and to smooth dry skin.

Example 2

Moisturizing Cream

The following composition is prepared in a way conventional to a person skilled in the art.

| Phase A | | |
|---|---|---|
| Demineralized water | q.s. for | 100% |
| Preservatives | | 0.5% |
| Carbomer | | 0.4% |
| Glycerol | | 7.0% |
| Phase B1 | | |
| Oxyethylenated (200 EO) sorbitan stearate | | 0.9% |
| Phase B2 | | |
| PEG-100 stearate and glyceryl stearate | | 2.1% |
| Isononyl isononanoate | | 10.0% |
| Petroleum jelly | | 2.0% |
| Octyldodecanol | | 10.0% |
| Androst-5-en-17-one, 3-(acetyloxy)-7-methoxy-, (3β, 7α) | | 0.5% |
| Butylated hydroxytoluene | | 0.1% |
| UV screening agent | | 1.0% |
| Ceramides | | 0.5% |
| Phase C | | |
| Water | | 2.0% |
| Triethanolamine | | 0.5% |
| Urea | | 1.0% |

This cream can be used for caring for dry skin.

Example 3

Antiageing Cream

| | | |
|---|---|---|
| Acrylate/$C_{10-30}$ acrylate copolymer | | 0.5% |
| Water | | 12.0% |
| Isononyl isononanoate | | 5.0% |
| Androst-5-ene-7,17-dione, 3-(acetyloxy), 17-oxime, (3β) | | 0.1% |
| Cyclohexasiloxane | | 5.0% |
| Octyl methoxycinnamate | | 1.0% |
| Triethanolamine | | 1.0% |
| Glycerol | | 6.0% |
| Preservatives | | 0.5% |
| Polyacrylamide and $C_{13-14}$ isoparaffin and laureth-7 | | 1.0% |
| Water | q.s. for | 100% |

This composition can be prepared in the following way. The polymer of phase A is dispersed in water at 40° C. The constituents of phase B are heated at 70° C. until completely dissolved and then the temperature is brought back to 40° C. The constituents of phase C are mixed at 50° C. Phase B is subsequently introduced into phase A at 40° C. with stirring and then phase C is added to them.

This cream can be used in once or twice daily applications to treat cutaneous signs of ageing, in particular to fade out wrinkles and fine lines.

Example 4

Antiageing Cream

The following composition is prepared in a way conventional to a person skilled in the art.

| Phase A | | |
|---|---|---|
| Demineralized water | q.s. for | 100.0% |
| Preservatives | | 0.5% |
| Carbomer | | 0.4% |
| Glycerol | | 7.0% |
| Phase B1 | | |
| Oxyethylenated (200 EO) sorbitan stearate | | 0.9% |
| Phase B2 | | |
| PEG-100 stearate and glyceryl stearate | | 2.1% |
| Isononyl isononanoate | | 10.0% |
| Octyldodecanol | | 10.0% |
| Androst-5-ene-7,17-dione, 3-(acetyloxy), 17-oxime, (3β) | | 0.1% |
| Butylated hydroxytoluene | | 0.1% |
| UV screening agent | | 1.0% |
| Phase C | | |
| Water | | 2.0% |
| Triethanolamine | | 0.5% |
| Extract of *Centella asiatica* | | 1.0% |
| Palmitoyl pentapeptide (Matrixyl ® from Sederma) | | 0.1% |

This cream is of use as firming day cream.

Example 5

Cleansing Gel for Greasy Skin

The following composition is prepared in a way conventional to a person skilled in the art:

| | |
|---|---|
| Lauryl phosphate | 6.50% |
| Decyl glucoside | 16.25% |
| Polyquaternium-7 | 5.70% |
| Oxyethylenated (150 EO) pentaerythrityl tetrastearate | 0.50% |
| Glycerol | 3.50% |
| Sorbitol | 3.50% |
| Potassium hydroxide | 1.70% |
| Hydroxypropylcellulose | 0.20% |
| Disodium EDTA | 0.05% |
| Sodium chloride | 0.10% |
| Androst-5-en-17-One, 3-(acetyloxy)-7-fluoro-, (3β, 7β) | 0.5% |
| Preservatives | 0.30% |
| Water | q.s. for 100% |

This gel makes it possible to regulate sebum secretions and to tone down skin imperfections.

Example 6

Antiblemish Patch

A patch comprising the following composition is prepared:

| | |
|---|---|
| Water | 40.0% |
| Alcohol | q.s. for 100% |
| Glycerol | 7.0% |
| Androst-5-en-17-one, 3-(acetyloxy)-7-fluoro-, (3β, 7β) | 0.1% |
| Poly (vinyl alcohol) | 5.0% |
| Kojic acid | 0.5% |

This patch can be applied to the hands and to the area above the neckline to fade out pigmentary blemishes, in particular blemishes due to ageing.

Example 7

Hair Lotion for Combating Hair Loss

The following composition is prepared in a way conventional to a person skilled in the art:

| | |
|---|---|
| Water | 25.0% |
| Glycerol | 7.0% |
| Androst-5-ene-7,17-dione, 3-(acetyloxy)-, 17-oxime, (3β) | 0.5% |
| Alcohol | q.s. for 100% |

This lotion is effective in preventing hair loss.

The present application claims priority from French patent application no. 0113817, filed Oct. 25, 2001, the entire disclosure of which is hereby incorporated by reference. Also, all publications, patents and other documents disclosed herein are hereby incorporated by reference as well.

What is claimed is:

1. A method for improving the appearance of a keratinous substance comprising applying to said keratinous substance at least one DHEA derivative of the following formula (I):

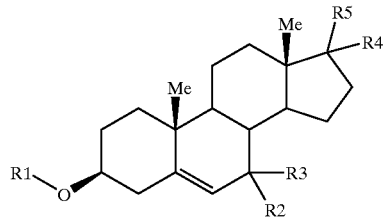

in which:

R1 is selected from the group consisting of
(a) a hydrogen atom;
(b) a saturated or unsaturated, linear or branched, or cyclic, which can optionally comprise one or more heteroatoms, alkyl group which is optionally substituted by one or more groups selected from the group consisting of —OR', —SR', —COOR',—NR'R', halogen, perfluoroalkyl, sulphate, phosphate, aryl, heterocycle, and mixtures thereof;
(c) an alkylcarbonyl group, the alkyl part of which is saturated or unsaturated, linear, branched or cyclic, and optionally substituted by one or more groups selected from the group consisting of —OR', —SR', —COOR', —NR'R', halogen, perfluoroalkyl, sulphate, or phosphate, aryl, heterocycle, and mixtures thereof;
(d) a phenyl group, optionally substituted by one or more groups selected from the group consisting of —OR', —SR', —COOR', —NR'R', halogen, perfluoroalkyl, sulphate, phosphate, aryl, heterocycle groups, and mixtures thereof;
(e) a benzyl group, optionally substituted by —OR', —SR', —COOR', —NR'R', halogen, perfluoroalkyl, sulphate, phosphate, aryl, heterocycle groups, and mixtures thereof;
(f) an arylcarbonyl group or an arylalkylcarbonyl group optionally substituted by one or more groups selected from the group consisting of —OR', —SR', —COOR', —NR'R', halogen, perfluoroalkyl, sulphate, phosphate, aryl, heterocycle groups, and mixtures thereof;
(g) an O=P (OH) OR' group;
(h) an (O)$_2$SOR' group;
(i) an (O)$_2$SR' group;
(j) a trialkylsilyl group (SiR'$_3$) in which the R' groups may be identical or different;
(k) an alkyloxycarbonyl group (R'OCO);
(l) an alkylaminocarbonyl group (R' NR''' CO); and
(m) a carbohydrate comprising 3 to 100 carbon atoms;
R4 and R5:
(a) together represent a group selected from the group consisting of
(1) a keto group (=O);
(2) a =CHR' group;
(3) an =NR' group; and
(4) a =NCOR' group;
(b) each represent an identical —OR'' group;
(c) each represent an identical or different group selected from the group consisting of
(1) a hydrogen atom;
(2) an —NR'R' group; and
(3) an —NHCOR' group;
R1 and R3 are defined as follows:
(a) when R2 is a hydrogen atom, and R3 is an —OR6 group in which R6 is selected from the group consisting of alkyl, benzyl and phenyl; or (b) R2 and R3 each represent an —OR" group in which each of the R" groups represents an alkyl group;

R' is selected from the group consisting of a hydrogen atom and a saturated or unsaturated, linear or branched, or cyclic, which can optionally comprise one or more heteroatoms, alkyl group optionally substituted by one or more —OR''', —COOR''', halogen, and —NR'''R''' groups; or an aryl group, optionally substituted by one or more —OR''', —COOR''', halogen, and —NR'''R''' groups;

R''' represents a hydrogen atom or a saturated or unsaturated and linear, branched or cyclic alkyl chain; wherein in each of the —NR'R' and —NR'''R''' groups, the R' and R''' substituents are identical or different.

2. The method according to claim 1, wherein the DHEA derivative comprises R1 which is a saturated or unsaturated, linear or branched, or cyclic, which can optionally comprise one or more heteroatoms, $C_1$–$C_{12}$ alkyl group optionally substituted by one or more groups selected from the group consisting of —OR', —SR', —COOR', —NR'R', halogen, and mixtures thereof.

3. The method according to claim 1, wherein the DHEA derivative comprises R1 which is a saturated or unsaturated, linear or branched, or cyclic, which can optionally comprise one or more heteroatoms, $C_1$–$C_6$ alkyl group optionally substituted by one or more groups selected from the group consisting of —OR', —SR', —COOR', —NR'R', halogen, and mixtures thereof.

4. The method according to claim 1, wherein the DHEA derivative comprises R1 which is substituted with a heterocycle selected from the group consisting of an indole, a pyrimidine, a piperidine, a morpholine, a pyran, a furan, a piperazine, and a pyridine.

5. The method according to claim 1, wherein the DHEA derivative comprises R1 which is a $C_1$–$C_{24}$ alkylcarbonyl group, the alkyl part of which is saturated or unsaturated and linear, branched or cyclic and optionally substituted by one or more groups selected from the group consisting of —OR', —SR', —COOR', —NR'R', halogen, and mixtures thereof.

6. The method according to claim 5, wherein R1 is an alkylcarbonyl group with a $C_6$–$C_{18}$ alkyl part.

7. The method according to claim 1, wherein the DHEA derivative comprises R1 which is a phenylcarbonyl or a benzylcarbonyl.

8. The method according to claim 1, wherein the R' and R''' groups are selected from the group consisting of a hydrogen atom and a $C_1$–$C_6$ alkyl group.

9. The method according to claim 1, wherein the R' and R''' groups are selected from the group consisting of a hydrogen atom, a methyl group, an ethyl group, a butyl group, a propyl group, an isopropyl group and a tert-butyl group.

10. The method according to claim 1, wherein the —NR'R' and —NR'''R''' groups are amino acids.

11. The method according to claim 10, wherein the —NR'R' and —NR'''R''' groups are selected from the group consisting of L-alanine, L-arginine, L-asparagine, L-aspartic acid, L-cysteine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine.

12. The method according to claim 1, wherein the DHEA derivative of formula (I) is selected from the group consisting of (1) Androst-5-en-17-one, 3-(acetyloxy)-7-methoxy-, (3β, 7α);

(2) Androst-5-en-17-one, 3-(acetyloxy)-7-methoxy-, (3β, 7β);

(3) Androst-5-en-17-one, 3-hydroxy-7-methoxy-, (3β, 7α); and (4) Androst-5-en-17-one, 3-hydroxy-7-methoxy-, (3β, 7β).

13. The method according to claim 1, wherein the method comprises treating cutaneous signs of ageing.

14. The method according to claim 1, wherein the method comprises treating a faded complexion.

15. The method according to claim 1, wherein the method comprises treating disorders of pigmentation of the skin or hair.

16. The method according to claim 1, wherein the method comprises treating sensitive skin and/or dandruff and/or drying of the skin.

17. The method according to claim 1, wherein the method comprises treating hyperseborrhoea and/or imperfections related to hyperseborrhoea.

18. The method according to claim 1, wherein the method comprises treating hair loss and/or canities.

19. The method according to claim 13, wherein the cutaneous signs of ageing are selected from the group consisting of wrinkles, fine lines, cutaneous atrophy, loss of firmness and/or of elasticity of the skin, an uneven skin grain with presence of dilated pores, and loss of radiance of the skin and/or pigmentary blemishes.

20. A composition comprising, in a physiologically acceptable medium, at least one DHEA derivative according to claim 1 and at least one compound selected from the group consisting of a desquamating agent, a moisturizing agent, a depigmenting or propigmenting agent, an antiglycation agent, an NO-synthase inhibitor, a 5α-reductase inhibitor, a lysyl and/or prolyl hydroxylase inhibitor, an agent which stimulates the synthesis of dermal or epidermal macromolecules and/or which prevents their decomposition, an agent which stimulates the proliferation of fibroblasts and keratinocytes and/or the differentiation of keratinocytes, a muscle relaxant, a compound which reduces irritation of neurogenic origin, an antimicrobial agent, a tightening agent, an agent for combating pollution or free radicals, and a soothing agent capable of inhibiting at least one enzyme.

21. A cosmetic composition comprising, in a physiologically acceptable medium, at least one DHEA derivative according to claim 1 and at least one optionally coated inorganic pigment and/or at least one UV screening agent selected from the group consisting of (a) a benzophenone derivative;

(b) a triazine derivative;

(c) benzene-1,4-di(3-methylidenecamphor-10-sulphonic acid), optionally in the partially or completely neutralized form;

(d) a salicylic acid derivative;

(e) a cinnamic acid derivative;

(f) a liquid β,β-diphenylacrylate derivative;

(g) a p-aminobenzoic acid derivative;

(h) 4-methylbenzylidenecamphor;

(i) 2-phenylbenzimidazole-5-sulphonic acid;

(j) a 1,3,5-triazine derivative;

(k) a plant extract selected from the group consisting of an extract of *Rosmarinus officinalis*, of *Leontopodium alpinum* of *Leontopodium stracheyi*; and mixtures thereof; and (I) a benzotriazole silicone of formula:

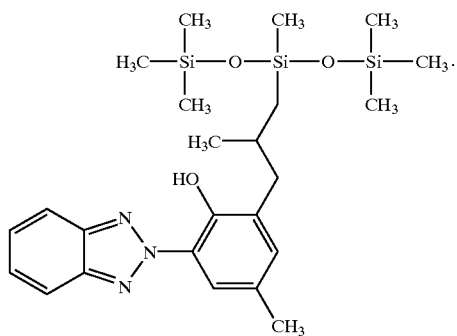

22. The composition according to claim 20, wherein 0.00001% to 100 by weight of the DHEA derivative with respect to the total weight of the composition is present.

23. The composition according to claim 21, wherein 0.00001% to 10% by weight of the DHEA derivative with respect to the total weight of the composition is present.

24. The composition according to claim 20, wherein from 0.001% to 5% by weight of the DHEA derivative with respect to the total weight of the composition is present.

25. The composition according to claim 21, wherein from 0.001% to 5% by weight of the DHEA derivative with respect to the total weight of the composition is present.

26. The composition according to claim 20, wherein from 0.1% to 0.5 by weight of the DHEA derivative with respect to the total weight of the composition is present.

27. The composition according to claim 21, wherein from 0.1% to 0.5% by weight of the DHEA derivative with respect to the total weight of the composition is present.

28. The method according to claim 1, wherein R3 is a methoxy group.

29. The method according to claim 1, wherein R1 is an alkylcarbonyl group.

30. The method according to claim 28, wherein R1 is an alkylcarbonyl group.

* * * * *

UNITED STATES PATENT AND TRADEMARK OFFICE
CERTIFICATE OF CORRECTION

PATENT NO. : 6,964,954 B2
DATED : November 15, 2005
INVENTOR(S) : Maria Dalko et al.

It is certified that error appears in the above-identified patent and that said Letters Patent is hereby corrected as shown below:

Column 24,
Line 64, "R1" should be -- R2 --.

Column 27,
Line 18, "100 by weight" should be -- 10% by weight --.

Signed and Sealed this

Fourteenth Day of February, 2006

JON W. DUDAS
*Director of the United States Patent and Trademark Office*